United States Patent [19]
Rattan

[11] Patent Number: 5,452,636
[45] Date of Patent: Sep. 26, 1995

[54] CUTTER ASSEMBLY

[75] Inventor: William Rattan, Cerritos, Calif.

[73] Assignee: Ethicon, Inc., Somerville, N.J.

[21] Appl. No.: 181,597

[22] Filed: Jan. 13, 1994

[51] Int. Cl.⁶ .................................................. B26D 7/01
[52] U.S. Cl. .................................. 83/385; 83/279; 83/454; 83/636; 83/950
[58] Field of Search ........................... 83/950, 623, 636, 83/385, 454, 649, 175

[56] References Cited

U.S. PATENT DOCUMENTS

| | | | |
|---|---|---|---|
| 284,496 | 9/1883 | Seymour | 83/636 |
| 1,651,834 | 12/1927 | Novick | 83/623 |
| 2,236,833 | 4/1941 | Pell et al. | 83/636 |
| 3,400,838 | 9/1968 | Leis et al. | 83/385 |
| 3,472,108 | 10/1969 | Vandersip | 83/950 |
| 3,611,551 | 10/1971 | Shave et al. . | |
| 3,980,177 | 9/1976 | McGregor . | |
| 4,072,041 | 2/1978 | Hoffman et al. . | |
| 4,694,718 | 9/1987 | Kinsley | 83/385 |
| 4,722,384 | 2/1988 | Matsutani . | |
| 4,806,737 | 2/1989 | Coates . | |
| 4,832,025 | 5/1989 | Coates . | |
| 4,922,904 | 5/1990 | Uetake et al. . | |
| 5,156,788 | 10/1992 | Chesterfield et al. | 264/157 |
| 5,226,336 | 7/1993 | Coates . | |

Primary Examiner—Kenneth E. Peterson

[57] ABSTRACT

A retractable cutter for cutting an indefinite length strand of suture material to a definite length while the strand is suspended under tension along a first axis, comprises a cutting blade mounted for at least reciprocal movement transverse to the first axis, from a first retracted position to a second cutting position. A support block is actuated to position the indefinite length strand for cutting thereof, and to support the strand as the cutting blade traverses the first axis as it reciprocates from the retracted position to the cutting position. The cutting blade is angled with respect to its reciprocating motion to effect a slice ratio of at least 1:1 as the blade cuts the supported suture strand at the cutting position to obtain a clean, broom-free cut.

23 Claims, 8 Drawing Sheets

CUTTER ASSEMBLY

FIELD OF THE INVENTION

The present invention relates generally to apparatuses for cutting material such as thread, rope, wire, and the like, and more specifically, to an apparatus for automatically cutting an indefinite flexible article, such as suture material, into strands of uniform length.

DESCRIPTION OF THE PRIOR ART

The medical products industry presently utilizes semi-automated procedures for swaging sutures to surgical needles. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to change the rack each time a different length of suture is desired.

In U.S. Pat. No. 4,922,904, the suture material is supplied wound on a bobbin and is fed through various guide means and a heater for straightening the material, prior to insertion within the crimping cavity of the surgical needle. In the embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly must be additionally fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

It would be far more desirable to provide a cutter assembly that is fully automated and which can automatically cut uniform lengths of suture material at high-speeds.

It would also be highly desirable to provide a cutter assembly that is retractable and will not interfere with the movement of gripper arms that pull the indefinite length strand of material prior to cutting thereof.

SUMMARY OF THE INVENTION

Accordingly, it is an object of the instant invention to provide a suture cutting apparatus that is fully automated and which can automatically and cleanly cut uniform lengths of suture material at high-speeds and without brooming of the suture tip.

It is another object of the instant invention to provide a cost-effective high-speed automatic cutter assembly that is retractable and will not interfere with the movement of gripper arms that pull the strand of indefinite length material along a single axis prior to cutting thereof.

Yet another object of the instant invention is to provide a cutter assembly that is mounted on a movable carrier that provides an apparatus for heat tipping the strand of suture material to be cut.

These and other objects of the present invention are attained with a retractable cutter for cutting an indefinite length strand of suture material to a definite length while the strand is suspended under tension along a first axis. A cutting blade is mounted for at least reciprocal movement transverse to the first axis, from a first retracted position to a second cutting position. A support block is actuated to position the indefinite length strand for cutting thereof, and to support the strand as the cutting blade traverses the first axis as it reciprocates from the retracted position to the cutting position. The cutting blade is angled with respect to its reciprocating motion to effect a slice ratio of at least 1:1 as the blade cuts the supported suture strand at the cutting position to obtain a clean, broom-free cut.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENT

Figure 1:
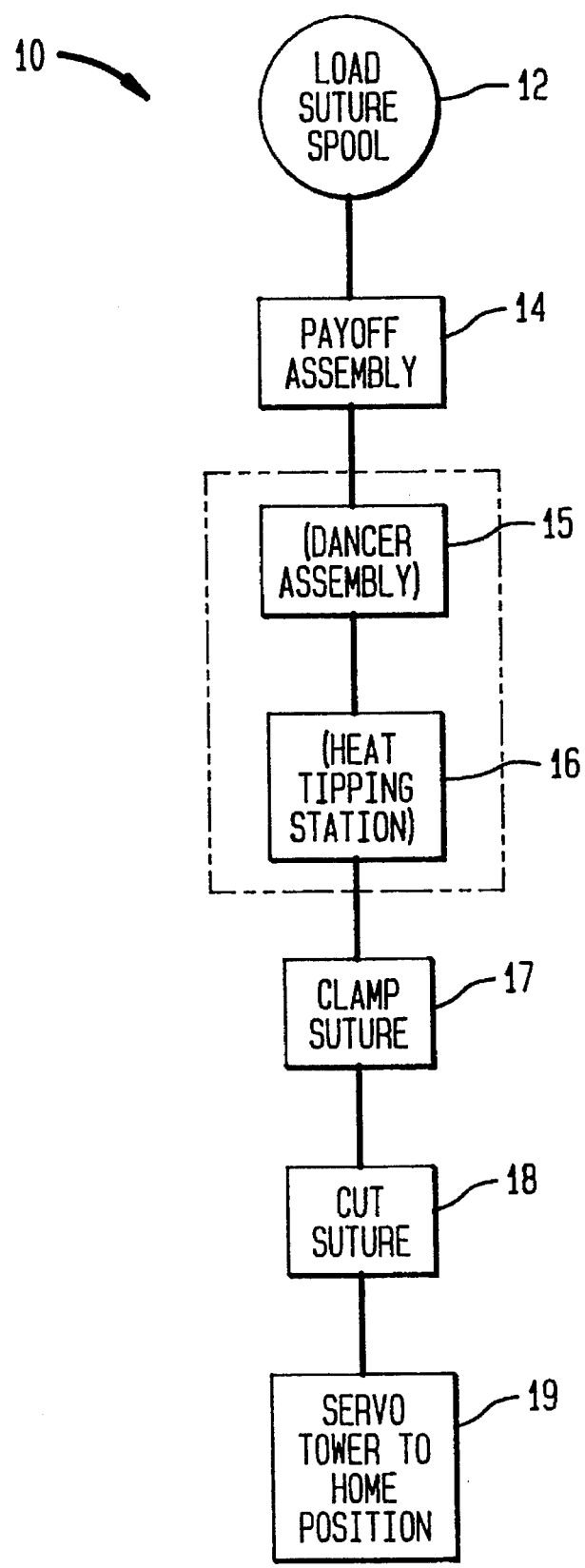
FIG. 1 is a block diagram showing the process used in the instant invention for unspooling, feeding, tipping, measuring, cutting, and delivering to a precise axial position, a length of material.

FIG. 1 is a block diagram generally illustrating the process 10 used to feed and cut a predetermined length of material. It should be understood that materials such as thread, wool, or wire of any gauge may be cut using the apparatus of the instant invention, however, the instant invention is preferably used to cut predetermined lengths of suture material prior to swaging the suture to a needle. A more detailed description of the needle threading and swaging system and the suture cutting system can be found in respective copending patent applications U.S. Ser. No. 08/181,598 and U.S. Ser. No. 08/181,595 assigned to the same assignee of the present invention. For descriptive purposes, the preferred embodiment discussed below is intended for cutting suture material used by medical personnel in hospitals and doctors' offices.

Generally, in the automatic cutting process 10 shown in FIG. 1, the suture material is supplied in various spools and configurations that may carry up to 5000 yards of material. This is indicated as step 12 in FIG. 1. Next, at step 14, the suture material is loaded into a payoff assembly which is part of a drawing tower apparatus to be described in detail below. This payoff assembly draws the suture material off the spool to enable cutting thereof. When larger spools of material are used, the material may be optionally loaded in a driven spool feed assembly with a dancer as indicated at step 15 to ensure that the material is not exposed to high tensions which could damage the material.

Some materials used in this device may require extra treatment or processing. For instance, as described in detail below, it may be desirable to heat the suture material under tension at the suture tip in order to stiffen the material to facilitate the insertion thereof within the suture receiving opening of a surgical needle. Thus, at optional step 16, heat may be applied at specific points along the length of suture material. At step 17 of the block diagram of FIG. 1, the suture material is held by a bottom movable gripper located at a lower portion of the drawing tower to maintain control of the indefinite length strand of material after the suture material above it is cut off as indicated at step 18. In a subsequent cycle, this lower gripper reciprocates to an upper position of the drawing tower while drawing the suture strand, while the top gripper descends, and the cycle is repeated as indicated at step 19 in FIG. 1. The process of advancing suture material 55 by alternating grippers at each cycle eliminates the recycle or return time for retaining the gripper to the original position. This makes faster machine speeds and hence, higher production rates possible. A detailed explanation of the apparatus used to carry out each step will be explained in further detail hereinbelow.

Figure 5:
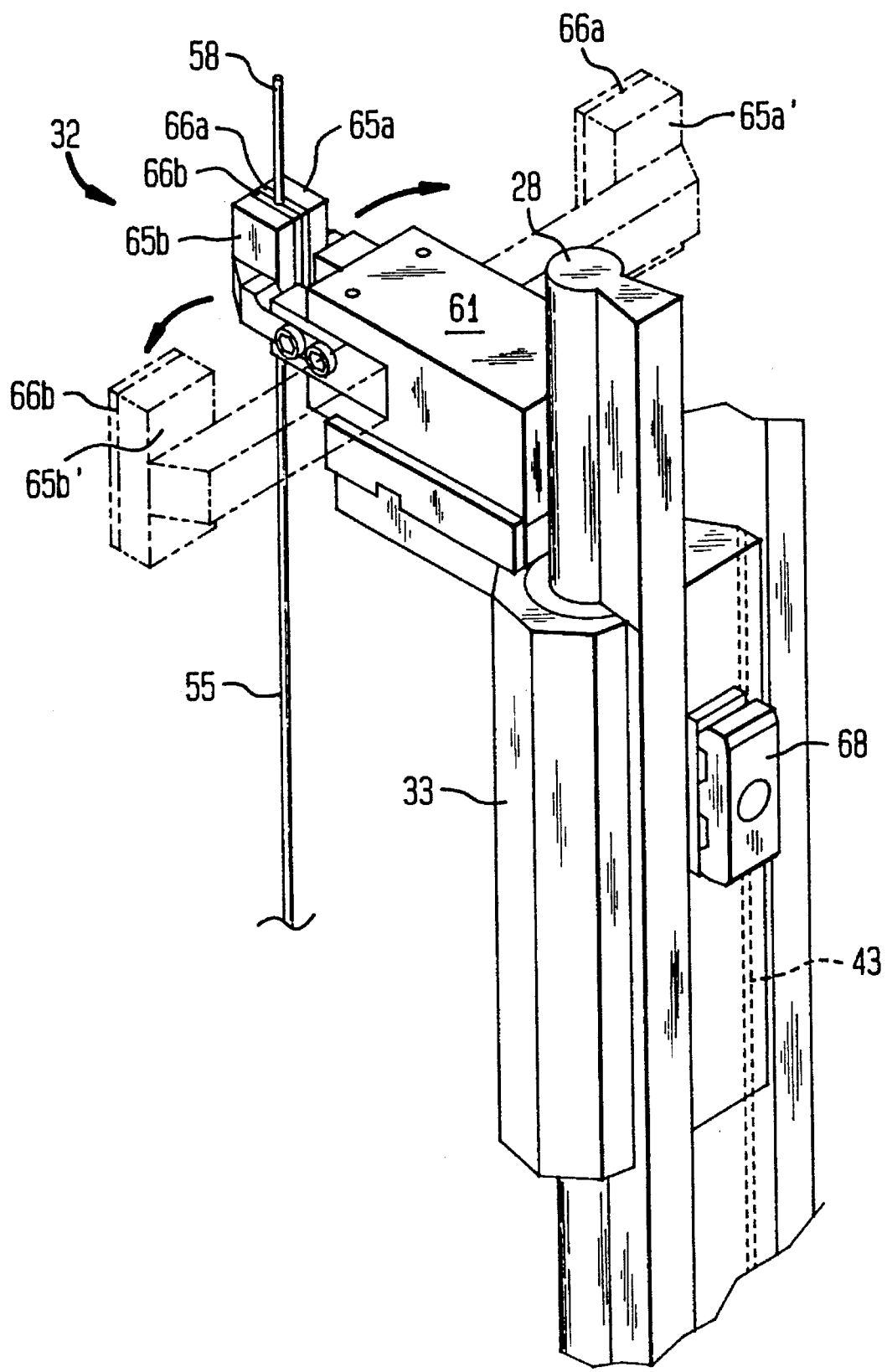
FIG. 5 is an enlarged view of a gripper assembly having gripper arms shown in their closed (suture gripping) and open positions.

The first step of the automatic cutting process 10 involves feeding the indefinite length suture material at one end of the payoff assembly. In the preferred embodiment, the payoff assembly is embodied as a drawing tower 20 shown in FIG. 2(*a*). The drawing tower 20 comprises left side rail 22 mounted on suitable left mounting block 23 and right side rail 24 mounted on suitable right mounting block 25 and defining a drawing frame for drawing an indefinite length of suture material along a drawing axis therebetween. Located parallel to the left and right side rails 22,24 and suitably connected thereto are respective left guide rod 26 and right guide rod 28. The first gripper means or right gripper 32 reciprocates up and down along right guide rod 28 while the second gripper means or left gripper 30 reciprocates up and down the left guide rod 26. Each of the grippers 30,32, as will be explained below, grip the suture material that is drawn from a spool through pulley 35 located at the bottom of the drawing tower 20, and carries the material to the upper end of the tower. The right gripper 32 is mounted on right gripper carrier 33 for vertical movement along right guide rod 28, and the left gripper 30 is mounted on left gripper carrier 31 for vertical movement along left guide rod 26 as shown in FIG. 2(*a*). FIG. 5 illustrates a gripper 32 (and 30)

having a gripper arm drive 61 that is pneumatically operated to drive pair of retractable gripper arms 65*a*, 65*b* toward each other to a suture gripping position, or, away from each other to an open position. Each retractable gripper arm is provided with a resilient, non-metallic pad 66*a*, 66*b* for gripping the tipped end 58 of the suture material 55 at an end thereof when actuated to the gripping position. To release the grip of the suture, gripper arms 65*a*,65*b* are retracted approximately 180 degrees apart in the direction indicated by the arrows of FIG. 5 to the open position. When in the open position the gripper arms 65*a*', 65*b*' do not interfere with the motion of the other vertically moving gripper as it reciprocates along the respective left or right rod carrying the next strand of suture material, nor will it interfere with the cutter assembly 200 as will be explained below. The retractable nature of the grippers and of the cutting assembly (discussed hereinbelow) enables the system to function alternately in opposing directions about a single suture axis.

As mentioned above, each gripper carrier and gripper thereof is designed to advance vertically along the respective left and right rods. As shown in FIG. 2(*a*), the right gripper 32 and gripper carrier 33 is driven by right servo motor 38 which is mounted to the right side rail 24 by right motor mounting bracket 39. Similarly, the left gripper 30 and gripper carrier 31 is driven by left servo motor 36 which is mounted to the left side rail 22 by left motor mounting bracket 37. In the preferred embodiment, both left and right servo motors are interfaced with and controlled by a control system computer, indicated generally as numeral 80 in FIG. 2(*a*), and as explained in further detail in copending patent application U.S. Ser. No. 08/181,607 assigned to the same assignee of the present invention. As shown in FIG. 2(*a*), right servo motor 38 drives timing belt 43 which consequently enables vertical positioning of right gripper carrier 33 along right rod 28, while the left servo motor 36 drives timing belt 41 which consequently enables vertical positioning of left gripper carrier 31 along left rod 26. As FIG. 5 illustrates, timing belt 43 is clamped to its respective gripper carrier 33 by a timing belt clamp 68 located on the back of the gripper carrier. A similar timing belt clamp (not shown) is provided on gripper carrier 31 for clamping timing belt 41 to enable vertical movement of gripper 30. FIG. 2(*a*) shows timing belt 41 engaging upper left pulley 45 and lower left pulley 46 as well as idler pulleys 47,48 which are part of tensioner block 44 that adjusts the tension of the timing belt 41 and consequently of left gripper carrier 31. Likewise, FIG. 2(*a*) shows timing belt 43 engaging upper right pulley 51 and lower left pulley 52 as well as idler pulleys 53,54 which are part of tensioner block 45 that adjusts the tension of the timing belt 43 and consequently of right gripper carrier 33.

Figure 3:
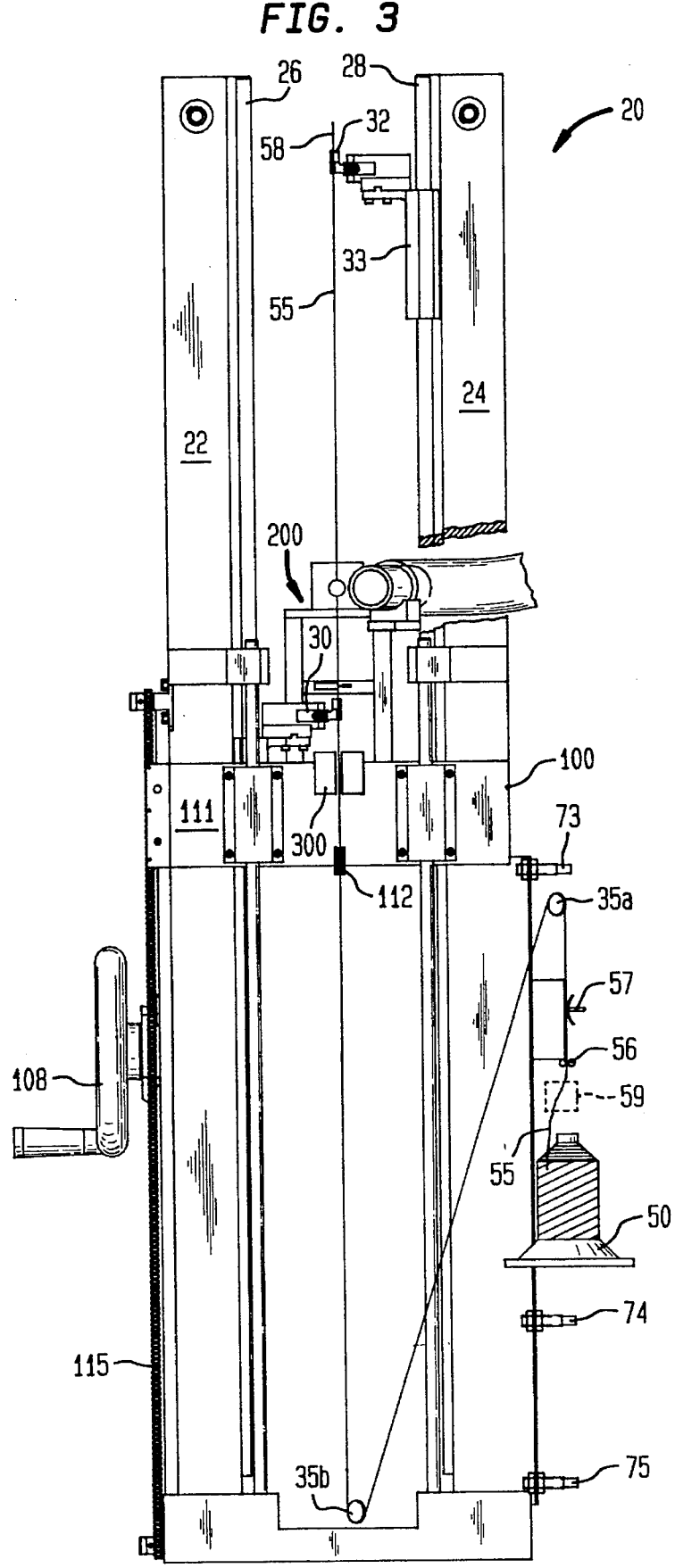
FIG. 3 is a detailed view of the servo tower illustrating cutter assembly 200 mounted on tip and cut carrier 100, and the king spool supplying the indefinite length strand of material.

FIG. 3 shows suture material 55 being pulled by right gripper 32 from a king spool 50. In an alternative embodiment, the spool may be motor driven in which case a dancer assembly 59 may be provided to control the tension of the material as it is being fed. To feed the indefinite length suture material to the drawing tower, the suture material 55 is first threaded through eyelet 56 to an optional knot detector 57 which senses any sudden change in the thickness of the suture material. Detection of a knot in material 55 will trigger the control system 80 to discard the cut strand of material at a subsequent operation. The suture material 55 is then advanced through the knot detector, over pulleys 35*a* and 35*b* located at the bottom of the drawing tower 20, and around pulley 112 which is mounted on the lower portion of tip and cut carrier 100 that is illustrated near the center of the tower in FIG. 3. As will be explained in detail below, and as illustrated in FIG. 3, the right gripper 32 grips the suture material 55 at a tipped portion below the end of tipped end 58.

Figure 2A:
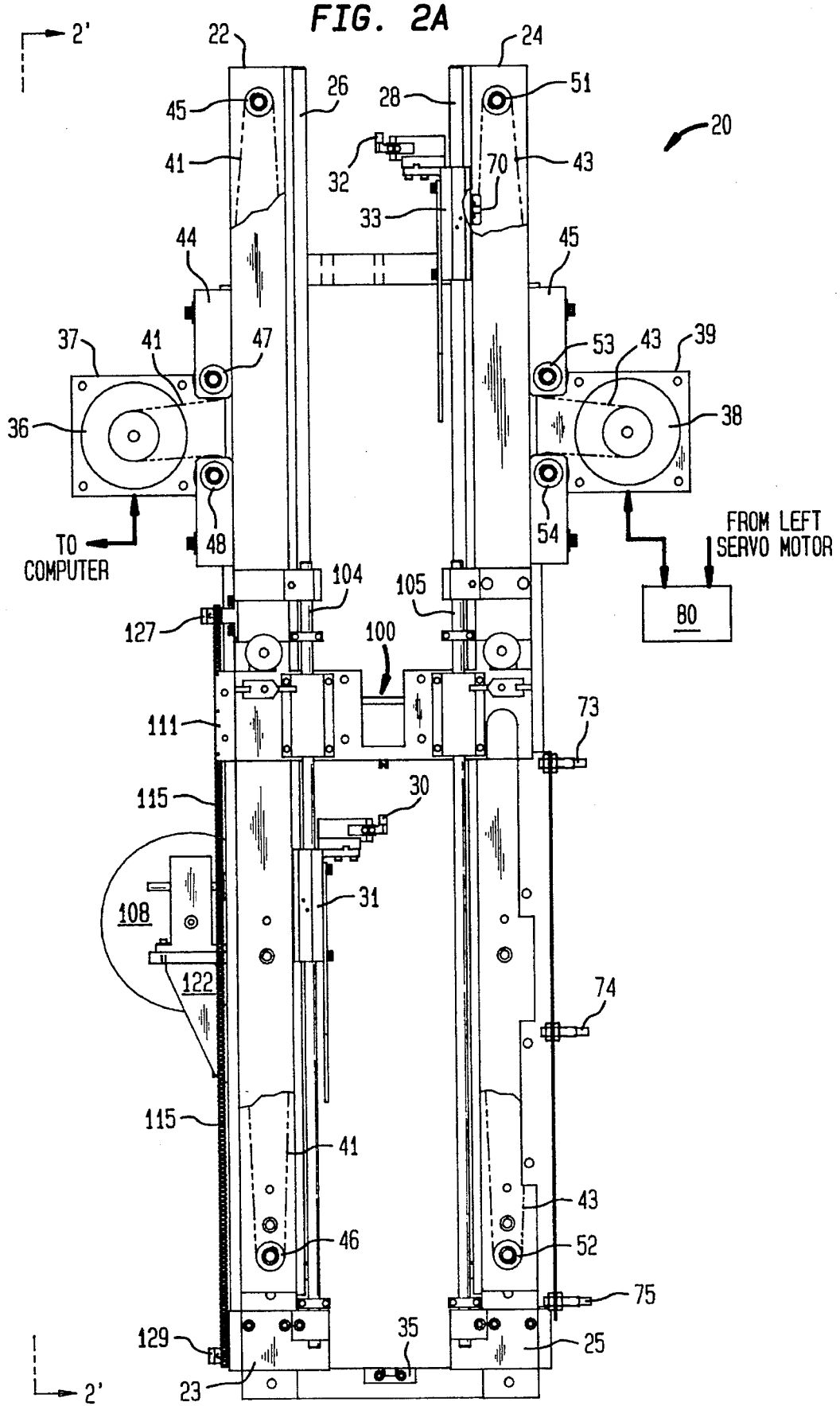
FIG. 2(a) is a detailed view of the cutting assembly tower of the instant invention.
Figure 4:
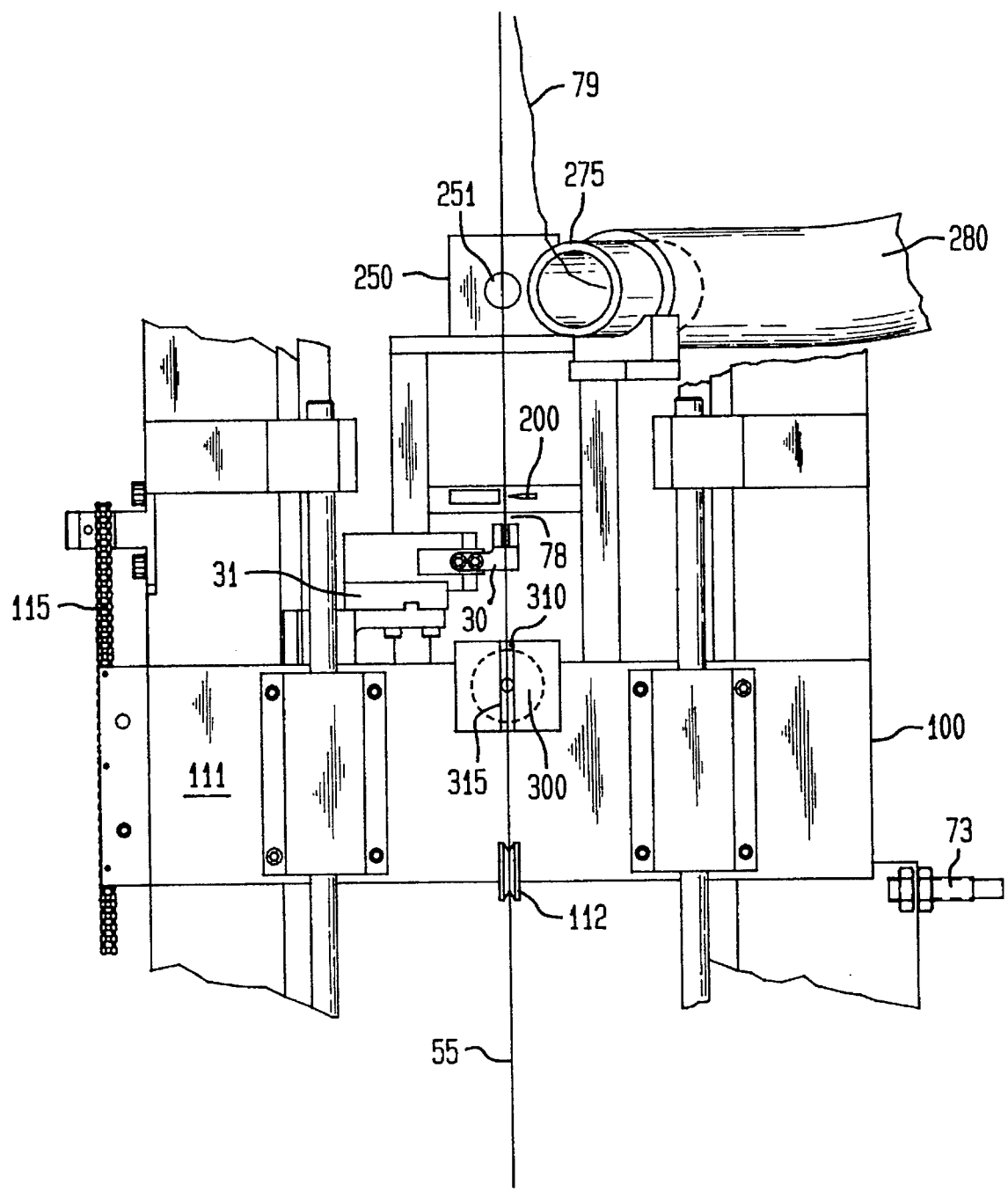
FIG. 4 is a detailed view of the tip and cut carrier 100 of the instant invention illustrating vacuum assembly 250 and tipping assembly 300 mounted thereon.
Figure 6:
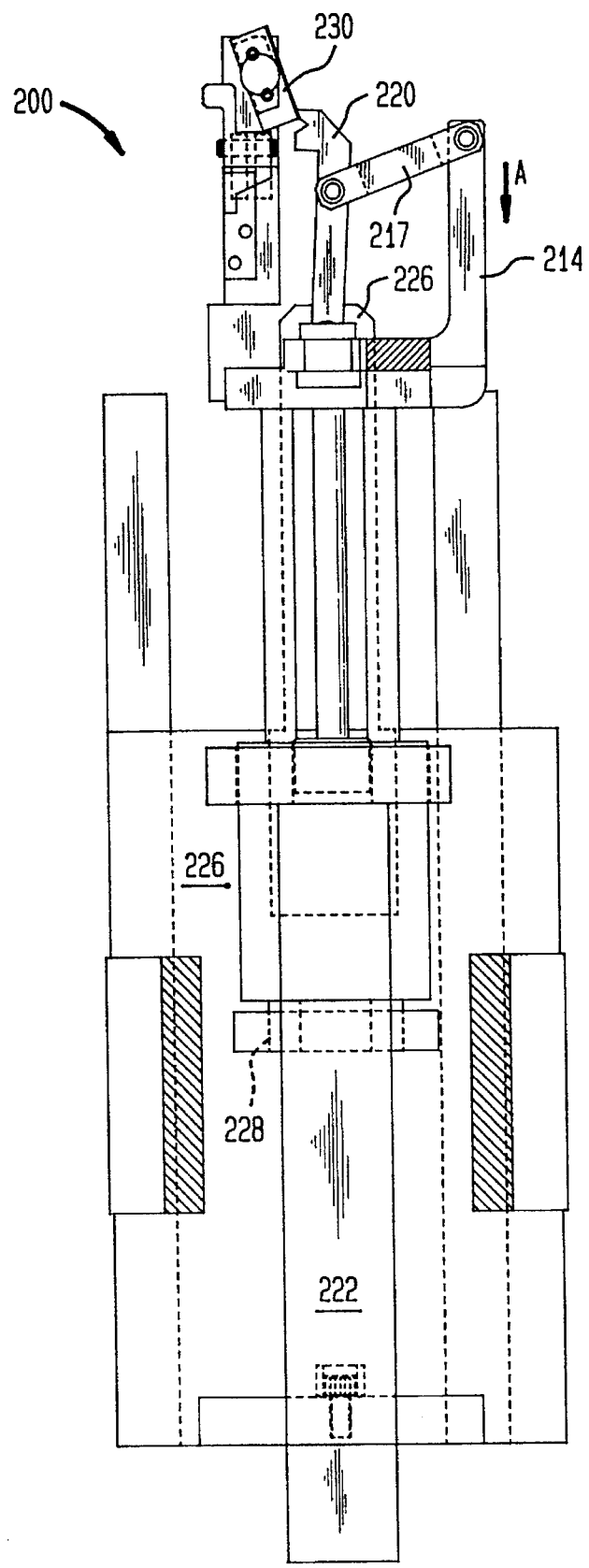
FIG. 6 is a detailed top view of the cutter assembly 200 for cutting flexible material in the instant invention.
Figure 7:
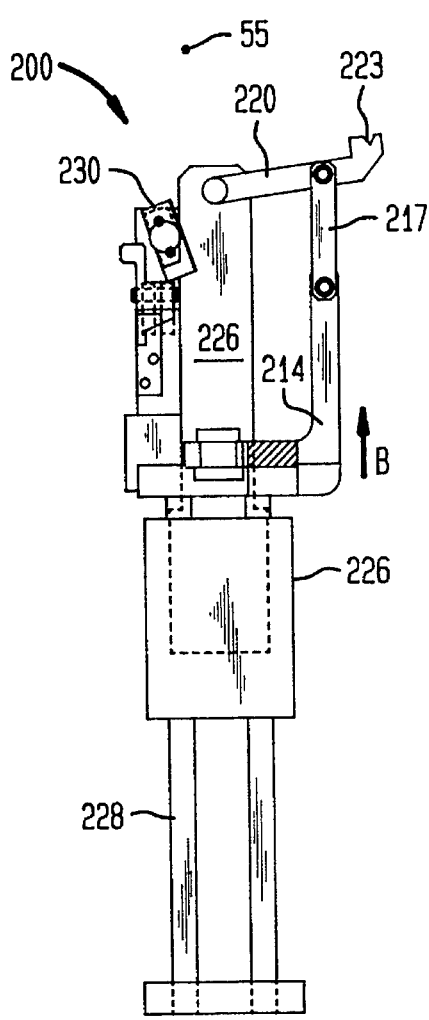
FIG. 7 is a detailed top view of the cutter assembly 200 shown in a fully retracted position.
Figure 8:
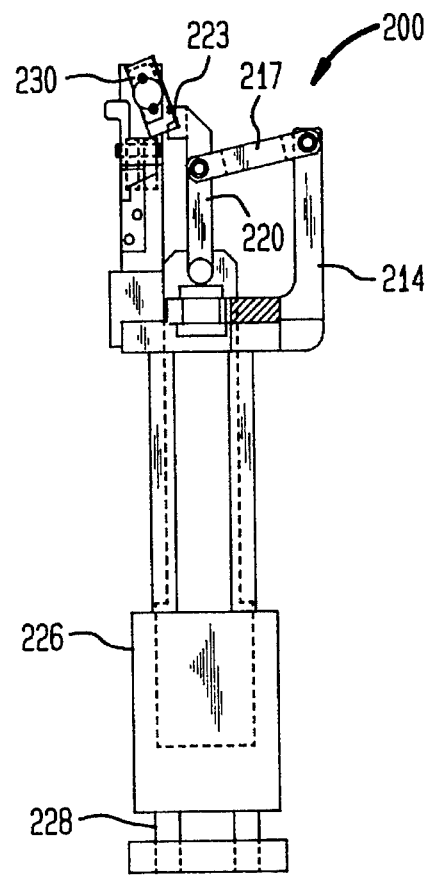
FIG. 8 is a detailed top view of the cutter assembly 200 shown in a fully extended (cutting) position.

As shown generally in FIGS. 3 and 4, tip and cut carrier 100 provides the support for tipping assembly 300 that applies heat to a specific location of the suture material, and also provides support for the cutter assembly 200 that cuts the suture material, as discussed in further detail with respect to FIGS. 6–8. FIG. 2(a) shows the tip and cut carrier 100 positioned along shafts 104 and 105 which are located parallel to respective left and right rods 26,28. In the preferred embodiment, vertical movement of the tip and cut carrier 100 is accomplished by cranking handwheel 108 shown in FIG. 2(b). Other embodiments may implement a computer controlled servo motor to vertically register the tip and cut carrier 100 prior to cutting the material. In the operation of the apparatus, both the stroke of the grippers 30,32 and the positioning of the tip and cut carrier 100 along drawing tower 20 dictates the length of the material that will be cut.

Figure 2B:
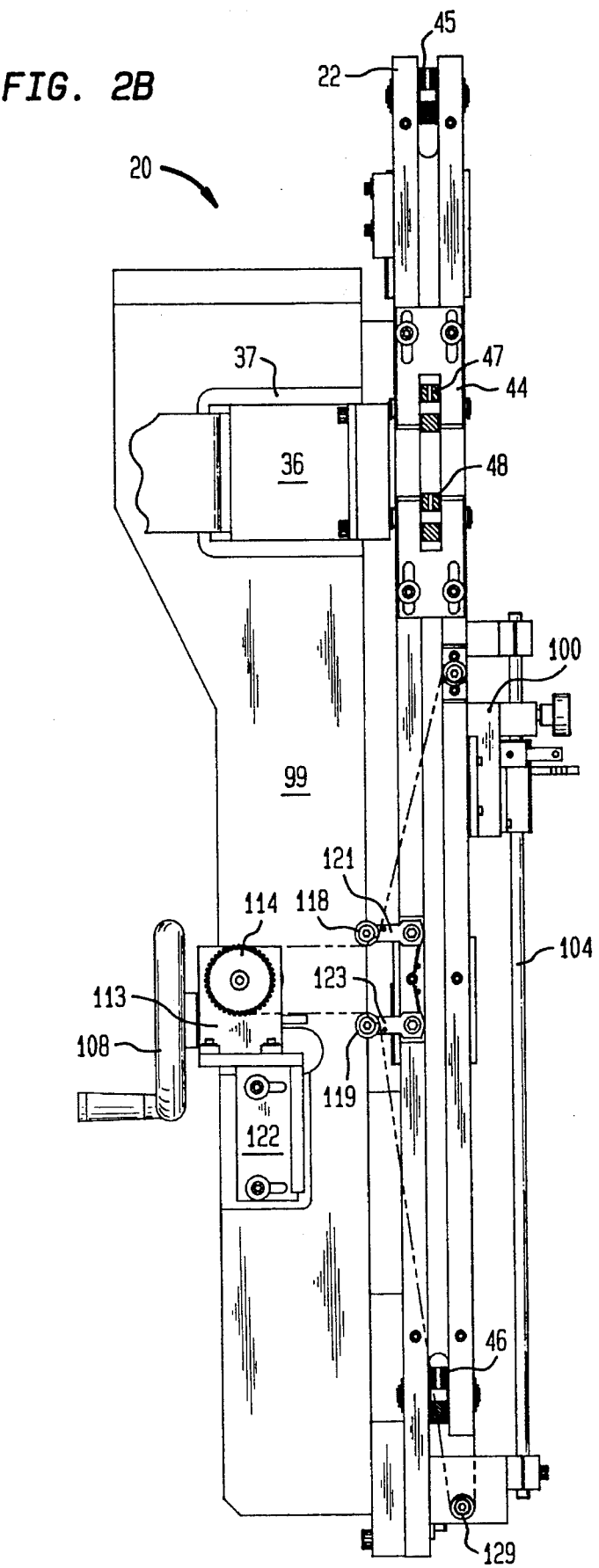
FIG. 2(b) is a detailed side view of the cutting assembly taken along line 2'—2' of FIG. 2(a) showing the pulley assembly for moving tip and cut assembly 100 of the instant invention.

As illustrated in FIG. 2(b), cranking handwheel 108 actuates a gearbox 113 that rotates chain drive sprocket 114. The gearbox 113 is mounted on a gearbox mounting bracket 122 which, in turn, is mounted to frame member 99. A cable chain 115 is engaged with chain drive sprocket 114 to actuate movement of the tip and cut carrier 100 as shown in FIG. 2(b). The cable chain 115 also engages chain idler sprockets 118 and 119 which are rotatably mounted to upper tensioner pulley bracket 121 and lower tensioner pulley bracket 123, respectively. The vertical positioning of tensioner pulley brackets 121,123 may be adjusted to vary the slack in cable chain 115. Cable chain 115 also engages chain idler sprockets 127 and 129 which are suitably mounted on left side rail 22. As shown in FIG. 3, the back 111 of tip and cut carrier 100 is clamped to cable chain 115.

As previously mentioned, tip and cut carrier 100 includes supports guide pulley 112 that positions the suture material 55. The suture material is received under tension from guide pulleys 35a,35b. As can be seen in FIG. 3, the lower threading pulley 35b, guide pulley 112, left gripper 30 and right gripper 32 are vertically aligned so that the cutter assembly 200 will always cut horizontally across the strand of material as will be explained below.

FIGS. 6–8 illustrate in detail the cutter assembly 200 which is suitably mounted to the tip and cut assembly 100 as shown in FIG. 4. As shown in FIG. 7, the cutter assembly comprises overcenter linkage 214 having a link arm 217 pivotally connected at one end thereof. A pivotal locator arm 220 is fixedly connected to link arm 217 at a second end thereof and is illustrated in FIG. 7 as substantially transverse thereto. The other end of locator arm 220 is pivotally connected to a stationary guide mechanism 226. Note, that all pivotal linkages described herein are simple pin linkages, the actuation of which creates the dwell moment for cutting the suture strand and obviates the need for complicated cam, slots, and sliding mechanisms.

As shown in FIG. 7, the stationary guide 226 is located in a plane perpendicular to the drawing axis of the suspended strand of material 55, and is located a distance from the strand approximately equivalent to the length of locator arm 220. In addition, overcenter linkage 214, locator arm 220, and cutting blade 230 all lie in planes perpendicular to the drawing axis of the strand of material 55.

A retractable ball slide 228 is mounted on the stationary guide 226 and coupled to overcenter linkage 214 for moving the overcenter linkage 214 and blade 230 along the stationary guide 226 in the direction indicated by arrow "A" in FIG. 6 from a cutting position to a retracted position shown in FIG. 7. As the ball slide 228 moves overcenter linkage 214 to a retracted position, the locator arm 220 is pivoted away from the strand 55 and the blade 230 is retracted. Thus, when the cutter assembly 200 is in the retracted position prior to cutting of the strand and immediately thereafter, the blade 230 and locator arm 220 do not interfere with the reciprocating motion of the grippers 30,32 along the drawing tower 20, nor do they come in contact with the suspended strand 55. In the preferred embodiment, pneumatic air cylinder 222 enables reciprocating movement of the ball slide 228 along stationary guide 226 as shown in FIG. 6.

When cutting the strand of material 55, the retractable ball slide 228 reciprocates in the direction toward the strand 55 indicated by arrow "B" in FIG. 7 to bring the overcenter linkage 214, and consequently the cutting blade 230 and locator arm 230 to the cutting position shown in FIG. 8. As the overcenter linkage 214 moves to the cutting position, the link arm 217 translates the movement of the ball slide 228 into pivotal movement of the locator arm 220. Locator arm 220 is provided with a Vee-shaped support notch 223 which functions to engage the strand of material 55 to be cut as the arm is pivoted into the cutting position. The Vee-shaped notch also functions to support the strand on two sides of the strand 55 while it is being horizontally cut on a third side. This enables clean, broom-free cuts especially of multifilament suture material, which has a tendency to form a broom end when the strand is under tension and is cut by a scissor device, or, when the multi-filament strand is sliced and not properly supported.

The cutting blade 230 of cutter assembly 200 is fixedly mounted to reciprocating ball slide 228 at a slight angle relative thereto and in a plane parallel with that of the locator arm 220. In the preferred embodiment, a single action by the pneumatic air cylinder 222 will enable movement of the ball slide 228 along stationary guide 226. This consequently enables pivoting of locator arm 220 from its retracted position (FIG. 7), so that Vee-shaped notch 223 supports the strand 55 at two sides thereof while a third side of the strand bears upon the cutting edge of blade 230 as the blade moves towards the supported strand 55 traversing the drawing axis thereof. Thus, the strand 55 is cut in a dwell moment of the locator arm after the locator arm 220 has pivoted in the direction toward the blade 230 to the cutting position shown in FIG. 8. The blade 230 slices the strand of material while it is held stationary by locator arm 220 by virtue of the angled orientation of the blade with respect to the axis of reciprocation illustrated in FIGS. 7 and 8. In the preferred embodiment, the slice ratio is 1:1, with the blade 230 angled at approximately 45 degrees relative to the axis of reciprocation, so that the strand 55 is cut an amount equivalent to the distance the blade 230 traverses the drawing axis.

Preparing a predetermined length of (suture) material for cutting and swaging is accomplished as follows:

First, the indefinite length strand of suture material 55 is manually threaded through eyelet 56, and about pulleys 35a, 35b, and 112. The first gripping means including right gripper 32 is actuated to the gripping position as illustrated in FIG. 5, so that the suture strand 55 will be gripped in the manner described above. Next, the gripper draws the material strand 55 to the top portion of the drawing tower as shown in FIG. 3. Then, operable under the control of the control system computer 80, the right servo motor 38 is enabled to drive the lead (right) gripper vertically along right rod 28 to a predetermined height, all the while drawing suture material 55 in the manner described above. As shown in FIG. 2(a), proximity sensor 70 is mounted at a position along the right side rail 24 to verify that right gripper 32 has reached a desired position and notify the control system 80 and servomotor 38 accordingly. Likewise, a proximity sensor (not shown) is mounted at the desired height along the left side rail 22 to verify that left gripper 30 has reached its desired location. As shown in FIG. 2(a), proximity sensors 73,74, and 75 are positioned vertically at different heights along the drawing tower 20 to additionally predetermine suture material lengths to be cut. Specifically, the locations of the proximity sensors 73,74, and 75 sense the positioning of the tip and cut assembly 100 as controlled by handcrank 108 to change the reciprocating travel of grippers 30,32.

In the preferred embodiment shown in FIG. 3, the lead gripper (gripper 32) grips the suture material on the tipped portion slightly below its tipped end 58 to register the tipped end for positioning within the suture receiving opening of a precisely registered surgical needle (not shown) for swaging thereof. To accomplish this, the lead gripper servomotor (for e.g., servomotor 38) advances the lead gripper for a long stroke distance, which may range from 12 inches to 36 inches depending upon the length of said suture strand desired, but is 16.1 inches in the preferred embodiment. The long stroke moves gripper 32 from a start position at the tip and cut carrier 100 to the position illustrated in FIG. 3. Simultaneously therewith, the other servomotor, for e.g., servomotor 36, positions the alternate gripper, for e.g., left gripper 30, along left rod 26 at a location preferably below the position of the cutter assembly 200 as shown in FIGS. 3 and 4. It is understood that the lead gripper is gripping the material 55 at all times during the long stroke, while the alternate gripper is in its open position and not gripping.

The next step, indicated in FIG. 1 as step 17, is to position the lead gripper 32 so that the tipped end 58 of the suture material is positioned within the suture receiving opening of a surgical needle for swaging thereof. To accomplish this, the lead gripper 32 must again advance the suture material 55 for a short stroke distance of about 1.9 inches, so that the tipped end 58 will advance precisely into the suture receiving opening of the surgical needle for a subsequent swaging operation to take place.

It should be understood that in another embodiment of the invention this step may consist of handing off the tip of the material to a subsequent material handling device, for e.g., connecting a length of wire to a wire harness, or the like.

As the tipped end 58 of the suture material is advanced during the short stroke distance prior to swaging, a tipped portion 78 of the material 55 that has been heated by tipping assembly 300, (explained hereinbelow), advances to a position slightly above the location of the left gripper 30 and adjacent the cutter assembly 200. Then, while the automatic swaging of the tipped end 58 to the surgical needle takes place at the top of the tower 20, the left gripper 30 (lower gripper) is actuated to grip the material 55 in the tipped portion 78, i.e., the portion of the suture material heated by tipping assembly 300 as shown in FIG. 4. Simultaneous with the engagement of gripper 30, the lead gripper 32 is actuated to release its grip on the suture material.

Figure 9:
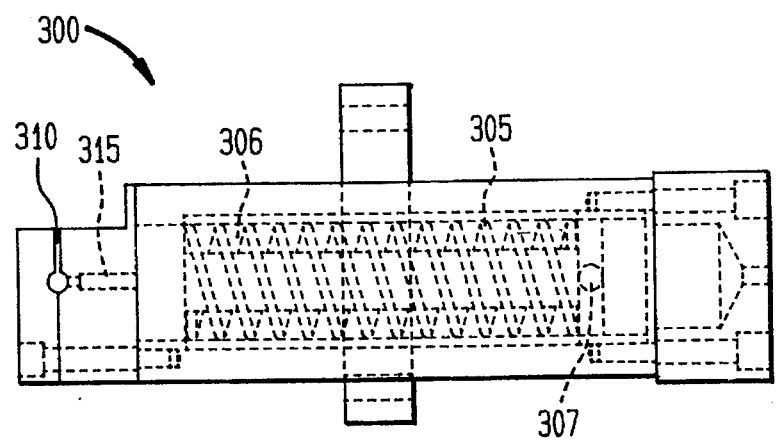
FIG. 9 is a detailed top view of the tipping assembly 300 for heating a portion of the suture material.

In the optional step indicated as step 16 FIG. 1, the right or lead gripper is halted after the long stroke so that a portion of the suture material 55 may be heated (tipped) prior to cutting thereof. Heating the suture under tension and the subsequent cooling thereof will stiffen the material and aid in the positioning and subsequent swaging of the tipped end of the material within the confines of the surgical needle. The operation of the tipping assembly 300 will now be explained as follows:

As shown in FIG. 9, the tipping assembly 300 is essentially an oven comprising a heat exchanger unit 305 that heats the air in the heater cavity 306. When a pulse of incoming air is provided to the heat exchanger input 307, the heated air is displaced and it provides a pulse of heated air to a vertical cylindrical cavity 310 as shown in FIG. 4 and in the top view of FIG. 9. As shown in FIG. 4 the heated air is forced through horizontal orifice 315 for a predetermined duration so that the length of suture material 55 suspended in tension through vertical cavity 310 will be heated. The control system computer 80 controls the duration of the heat pulse so that the material is adequately heated and will have sufficient time to cool before the cutting operation. Preferably, the tipping assembly 300 is located at a position that is located slightly below the alternate gripper. As mentioned above, this is required so that when the suture material 55 is advanced for insertion within the suture receiving opening of the needle during the short stroke, the tipped portion 78 that had been subject to the heated air will advance a corresponding length so that the alternate gripper, for e.g., left gripper 30, will now grip the material at the tipped portion 78. Therefore, when the strand is cut at the tipped portion 78, the indefinite length strand 55 having a new tipped end 58 will be subsequently advanced up the tower 20 by the left gripper 30 in the next cycle.

After swaging of the surgical needle takes place and the left gripper 30 has secured the suture strand 55, the strand is cut by the cutting assembly 200 in the manner described above and as indicated in step 18 in FIG. 1. In the preferred embodiment shown in FIG. 4, a vacuum air flow is energized to pull the strand of material 55 toward the nylon screen 251 to more precisely locate the suture strand in the target zone of the cutter. After cutting of the indefinite length suture material 55 at the tipped portion 78, the tail end 79 of the length of the cut suture material that had been swaged to the surgical needle is sucked into a large vacuum pipe 275, that is connected to a vacuum assembly 250 by vacuum hose 280 as shown in FIG. 4. The vacuum created in vacuum pipe 275 exerts a mild tension in the strand of material to keep the tail end from entanglement or coming into contact with the machinery. However, it is mild enough to allow the strand to be pulled out of the pipe 275 as the armed needle and suture are handed off for further downstream processes.

FIG. 4 shows the left gripper 30 positioned slightly below the cutter assembly 200 so that the strand will be gripped when the swaged strand is cut. Thus, the left gripper now grips the suture material 55 having a tipped end .58 and it now becomes the lead gripper. The next cycle begins with the left gripper vertically drawing the material 55 along the height of the drawing tower 20 for the long stroke to position the next strand to be cut for insertion within the surgical needle.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed is:

1. A retractable cutter for cutting an indefinite length strand of suture material to a definite length while said strand is suspended under tension along a first axis, said cutter comprising:

(a) a cutting blade having a cutting edge and mounted for reciprocal movement transverse to said first axis defined by said indefinite length strand from a first retracted position to a second cutting position;

(b) support block means mounted for reciprocating pivotal movement from a first retracted position to a second strand supporting position along a plane parallel to a plane defined by movement of said cutting blade to accurately position said indefinite length strand of suture material prior to cutting thereof, and for supporting said strand as the cutting blade traverses said first axis, whereby said edge of said cutting blade lies in said plane and is angled with respect to its reciprocating motion to effect a slice ratio of about 1:1 as said blade cuts said supported suture strand at said cutting position to obtain a clean, broom-free cut.

2. A retractable cutter for cutting an indefinite length strand of multi-filament suture material as claimed in claim 1, further comprising:

(a) a stationary guide means, said guide means positioned adjacent said indefinite length suture strand to be cut; and (b) an actuator means mounted on said stationary guide for providing at least reciprocal movement along a second axis transverse to said first axis;

wherein said cutting blade and said support block means are responsive to said reciprocating actuator to move from their respective first retracted positions to their respective second cutting and strand supporting positions.

3. The retractable cutter for cutting an indefinite length strand of suture material as claimed in claim 2 further including a locating arm having an effective length with said support block means located at one end thereof and having another end pivotally mounted to said stationary guide for providing said pivotal movement of said support block means from its first retracted position to its second strand supporting position in response to movement of said actuator.

4. The retractable cutter for cutting an indefinite length strand of suture material as claimed in claim 3 wherein said support block means is a V-shaped notch for supporting said suture strand on two sides during the cutting thereof.

5. The retractable cutter for cutting an indefinite length strand of suture material as claimed in claim 4 wherein said pivotal locating arm further comprises an over center link which isolates motion from said actuator means after said support block means has engaged said strand.

6. The retractable cutter for cutting an indefinite length strand of suture material as claimed in claim 5 wherein said over center link translates reciprocal movement of said actuator means into pivotal movement for said locating arm.

7. The retractable cutter for cutting an indefinite length strand of suture material as claimed 6, wherein said stationary guide is spaced a distance from said indefinite length strand as determined by the effective length of said pivotal locating arm.

8. The retractable cutter for cutting an indefinite length strand of suture material as claimed in claim 6, wherein said over center linkage further comprises first and second links, with said first link fixedly mounted on said actuator and said second link connecting said first link and said pivotal locating arm.

9. The retractable cutter for cutting an indefinite length strand of suture material as claimed in claim 2 further comprising a stationary blade holder mounted on said actuator for supporting said cutting blade during reciprocal motion thereof.

10. The retractable cutter for cutting an indefinite length strand of suture material as claimed in claim 2, wherein said cutting blade is angled with respect to said second axis to horizontally cut said strand with a slicing movement when said blade crosses said first axis.

11. The retractable cutter for cutting an indefinite length strand of suture material as claimed in claim 10, wherein said suture material is one of either mono-filament and multi-filament type.

12. A retractable cutter for cutting an indefinite length strand to length while said strand is suspended, said cutter comprising:

(a) a stationary guide means, said guide means positioned adjacent an indefinite length strand to be cut, said strand defining a first axis;

(b) an actuator mounted on said guide for providing at least reciprocal movement along a second axis;

(c) a pivotal locating arm having an effective length for positioning said indefinite length strand for cutting, said arm having a first end pivotally mounted along said second axis for pivoting from a first retracted position to a second strand engaging position in response to movement of said actuator;

(d) a cutting blade mounted for a least reciprocal movement across said first axis defined by said indefinite length strand, said cutting blade responsive to said reciprocating actuator to move from a first retracted position to a second cutting position;

whereby a single action by said actuator will first position said strand with said pivotal arm and then cut said strand with said cutting blade.

13. A retractable cutter as claimed in claim 12, wherein said first axis and said second axis are transverse to each another.

14. A retractable cutter as claimed in claim 12, wherein said cutting blade and said pivotal locating arm are both retracted behind said stationary guide when said pivotal locating arm is in its first retracted position.

15. A retractable cutter as claimed in claim 14, wherein said pivotal locating arm further comprises a support block means for supporting said strand during the cutting thereof.

16. A retractable cutter as claimed in claim 15, wherein said pivotal locating arm further comprises an over center linkage which isolates motion from said actuator after said pivotal locating arm has engaged said strand.

17. A retractable cutter as claimed in claim 16, wherein said over center linkage translates a reciprocal movement from said actuator into pivotal movement for said locating arm.

18. A retractable cutter as claimed in claim 17, wherein said stationary guide is spaced a distance from said indefinite length strand as determined by the effective length of said pivotal locating arm.

19. A retractable cutter as claimed in claim 17, wherein said over center linkage further comprises first and second links, with said first link fixedly mounted on said actuator and said second link connecting said first link and said pivotal locating arm.

20. A retractable cutter as claimed in claim 19, wherein said cutting blade is angled with respect to said second axis to horizontally cut said strand with a slicing movement when said blade crosses said first axis.

21. A retractable cutter as claimed in claim 16, wherein said actuator is mounted for reciprocal movement on said stationary guide.

22. A retractable cutter as claimed in claim 21, wherein said cutter further comprises a stationary blade holder mounted on said actuator for supporting said cutting blade during reciprocal motion thereof.

23. The retractable cutter for cutting an indefinite length strand of suture material as claimed in claim 15 wherein said support block means is a V-shaped notch for supporting said suture strand on two sides during the cutting thereof.

* * * * *

UNITED STATES PATENT AND TRADEMARK OFFICE
CERTIFICATE OF CORRECTION

PATENT NO.   : 5,452,636
DATED        : September 26, 1995
INVENTOR(S)  : William Rattan It is certified that error appears in the above-indentified patent and that said Letters Patent is hereby corrected as shown below:

Column 10, Line 47 - "14" should read "12"

Signed and Sealed this

Nineteenth Day of March, 1996

Attest:

BRUCE LEHMAN

Attesting Officer          Commissioner of Patents and Trademarks